(12) United States Patent
Luan et al.

(10) Patent No.: US 7,429,491 B2
(45) Date of Patent: Sep. 30, 2008

(54) RESTRICTED GLUCOSE FEED FOR ANIMAL CELL CULTURE

(75) Inventors: Yen-Tung Luan, Chelmsford, MA (US); Terry Cardoza Stanek, Tewksbury, MA (US); Denis Drapeau, Salem, NH (US)

(73) Assignee: Wyeth, Madison, NJ (US)

( * ) Notice: Subject to any disclaimer, the term of this patent is extended or adjusted under 35 U.S.C. 154(b) by 280 days.

(21) Appl. No.: 10/847,729

(22) Filed: May 17, 2004

(65) Prior Publication Data

US 2005/0070013 A1   Mar. 31, 2005

Related U.S. Application Data

(60) Provisional application No. 60/470,937, filed on May 15, 2003.

(51) Int. Cl.
*C12N 5/02* (2006.01)
(52) U.S. Cl. ..................... 435/404
(58) Field of Classification Search ........... 435/7.21, 435/70.1, 70.3, 139, 325, 375, 404, 408
See application file for complete search history.

(56) References Cited

U.S. PATENT DOCUMENTS

| | | | |
|---|---|---|---|
| 5,318,898 A | 6/1994 | Israel | 435/69.1 |
| 5,346,826 A * | 9/1994 | Andrews | 435/400 |
| 5,506,117 A * | 4/1996 | Andrews et al. | 435/29 |
| 5,618,924 A | 4/1997 | Wang et al. | 530/399 |
| 5,631,142 A | 5/1997 | Wang et al. | 435/69.1 |
| 5,856,179 A | 1/1999 | Chen et al. | 435/325 |
| 6,156,570 A | 12/2000 | Hu et al. | 435/375 |
| 6,180,401 B1 | 1/2001 | Chen et al. | 435/358 |
| 6,531,464 B1 * | 3/2003 | Szabo et al. | 514/183 |
| 2003/0087372 A1 * | 5/2003 | DelaCruz et al. | 435/69.1 |
| 2004/0048368 A1 | 3/2004 | Chen et al. | |
| 2006/0127975 A1 | 6/2006 | Link et al. | 435/69.1 |

FOREIGN PATENT DOCUMENTS

| | | |
|---|---|---|
| WO | WO 98/41611 | 9/1998 |
| WO | WO 02/101019 A2 | 12/2002 |
| WO | WO 2004/048556 A | 6/2004 |

OTHER PUBLICATIONS

Glacken et al., "Reduction of Waste Product Excretion via Nutrient Control: Possible Strategies for Maximizing Product and Cell Yields on Serum in Cultures of Mammalian Cells," *Biotechnol. Bioeng.* 28:1376-89 (1986).
Häggström et al., "Metabolic Engineering of Animal Cells," *Annals N.Y. Acad. Sci.*, 782:40-52 (1996).
Kurokawa et al., "Growth Characteristics in Fed-Batch Culture of Hybridoma Cells with Control of Glucose and Glutamine Concentrations," *Biotechnol. Bioeng.*, 44:95-103 (1994).
Ljunggren and Häggström, "Catabolic Control of Hybridoma Cells by Glucose and Glutamine Limited Fed Batch Cultures," *Biotechnol. Bioeng.*, 44:808-18 (1994).
Male et al., "On-Line Monitoring of Glucose in Mammalian Cell Culture Using a Flow Injection Analysis (FIA) Mediated Biosensor," *Biotechnol. Bioeng.*, 55:497-504 (1997).
Mather and Moore, "Culture media, animal cells, large scale production," *Encyclopedia of Bioprocess Technology: Fermentation, Biocatalysis, and Bioseparation*, vol. 2, Michael C. Flickinger and Stephen W. Drew, eds., John Wiley & Sons, Inc. (1999) pp. 777-785.
Siegwart et al., "Adaptive Control at Low Glucose Concentration of HEK-293 Cell Serum-Free Cultures," *Biotechnol. Prog.*, 15:608-16 (1999).
Zhou and Hu, "On-Line Characterization of a Hybridoma Cell Culture Process," *Biotechnol. Bioeng.*, 44:170-77 (1994).
ATCC product description for *Spodoptera frugiperda* cell line, "SF9 product description," printed Apr. 11, 2007.
ATCC product description for *Aedes aegypti* cell line, "*Aedes aegypti* product description," printed Apr. 11, 2007.
ATCC product description for *Aedes albopictus* cell line, "*Aedes albopictus* product description," printed Apr. 11, 2007.
ATCC product description for *Drosophila melanogaster* cell line, "Schneider's *Drosphila*Line 2 product description," printed Apr. 11, 2007.
ATCC product description for *Bombyx mori* cell line, "BM-N product description," printed Apr. 11, 2007.
ATCC product description for CHO (*Cricetulus griseus*) cell line, "CHO-K1 product description," printed Apr. 11, 2007.
ATCC product description for BHK (*Mesocricetus auratus*) cell line, "BHK-21 product description," printed Apr. 11, 2007.
ATCC product description for 293 (human) cell line, "293 product description," printed Apr. 11, 2007.
ATCC product description for FRhL-2 (*Macaca mulatta*) cell line, "DBS-FRhL-2 product description," printed Apr. 11, 2007.
ATCC product description for Sp2 (*Mus musculus*) cell line, "Sp2 product description," printed Apr. 11, 2007.
F-12K Medium formulation from ATCC, "F-12K Medium," found at http://www.atcc.org/common/documents/pdf/30-2004.pdf, printed Nov. 28, 2007, © Copyright 2002, 1 page.

* cited by examiner

*Primary Examiner*—Herbert J. Lilling
(74) *Attorney, Agent, or Firm*—Fitzpatrick, Cella, Harper & Scinto

(57) ABSTRACT

Methods of improving protein production in animal cell cultures are provided. Cell culture methods are presented wherein glucose is fed in a restricted manner to cell culture; this restricted feeding of glucose to the cell culture results in lactate production being controlled to a low level. The restricted feeding of glucose in a fed-batch process is not accomplished through a constant-rate feeding of glucose, and the restricted feeding need not depend on sampling. Instead, restricted feeding of glucose to the culture is accomplished through feeding of glucose to the culture at a rate that is a function of an expected or a premodeled rate of glucose consumption by the animal cells when exposed to medium containing a high level of glucose. Because lactate production is controlled to low levels, recombinant protein production is increased.

32 Claims, 9 Drawing Sheets

Cell Concentration:
Control vs. Expected Increase Feed

Cell Concentration:
Control vs. Premodeled Feeds

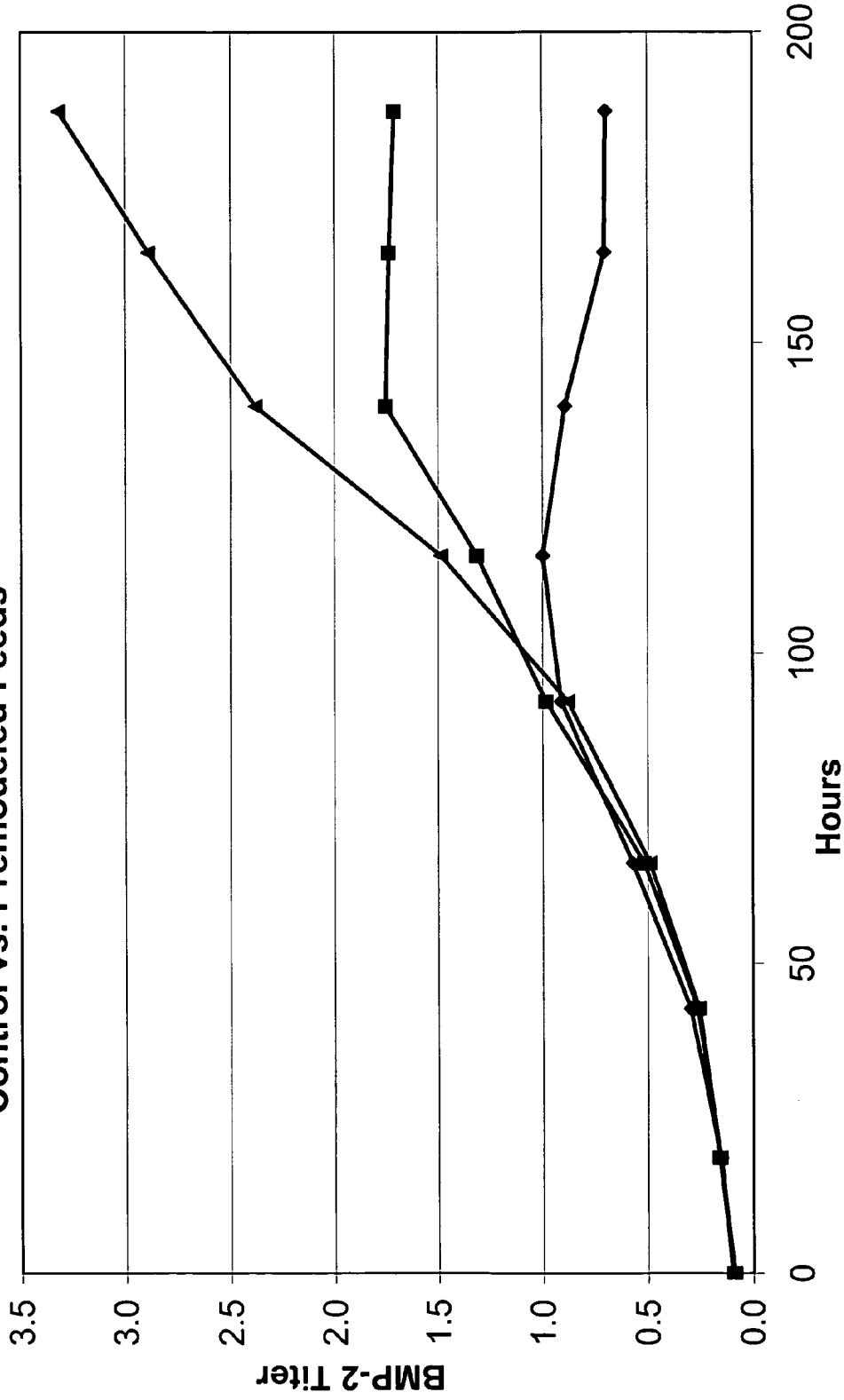

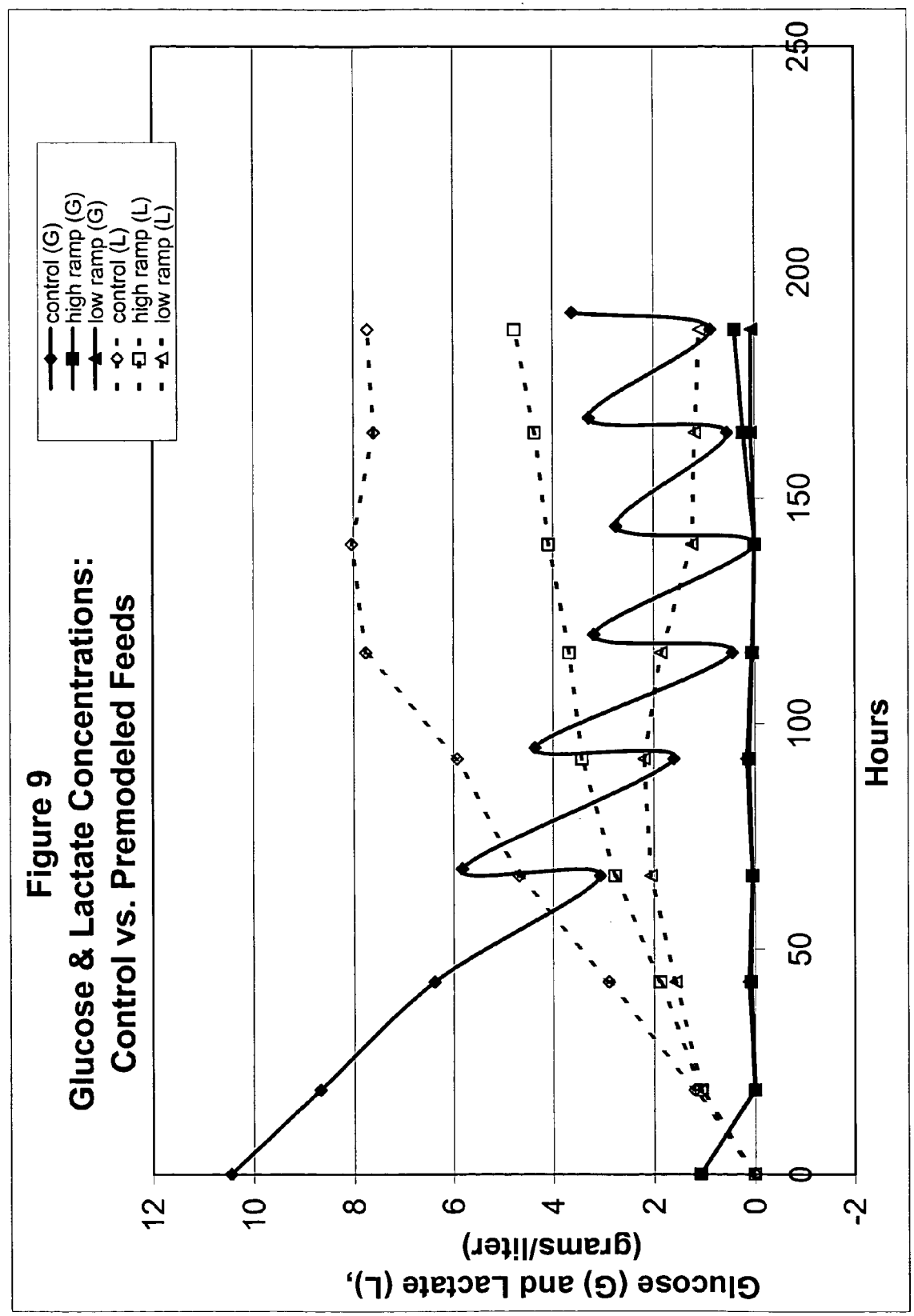

RESTRICTED GLUCOSE FEED FOR ANIMAL CELL CULTURE

PRIOR RELATED APPLICATIONS

This application claims the benefit of U.S. Provisional Application Ser. No. 60/470,937, filed May 15, 2003, which is incorporated herein by reference in its entirety.

BACKGROUND OF THE INVENTION

1. Field of the Invention

The invention relates to a method of improving protein production by cultured animal cells. More specifically, the invention relates to a method for controlling lactic acid production by cultured animal cells (preferably mammalian cells) to low levels in a fed-batch cell culture. In some embodiments, the invention provides methods of maintaining lactate production by cultured cells at low levels through the use of glucose delivery systems that do not rely on the sampling of cultures at regular intervals. In particular, the invention relates to culturing animal cells under conditions wherein glucose is fed to or into the culture in a restricted manner, e.g., at a rate that is a function of an expected or a premodeled rate of glucose consumption by the animal cells when they are exposed to a medium containing a high level of glucose. In association with this restricted feeding, the production by cultured cells of lactic acid is controlled to a low level during culture. As an end result, recombinant protein production from the cultured cells is increased, for example, in order to facilitate commercial-scale production.

2. Related Background Art

A large proportion of biotechnology products, whether commercially available or only in development, are protein therapeutics. Furthermore, the cellular machinery of an animal cell (versus a bacterial cell) generally is required in order for many forms of protein therapeutics (such as glycosylated proteins or hybridoma-produced monoclonal antibodies (MAbs)) to be produced. Consequently, there is an increasing demand for production of these proteins in animal cell cultures.

As compared to bacterial cell cultures, however, animal cell cultures have lower production rates and typically generate lower production yields. Maintaining glucose concentrations in cell culture media at low concentrations (e.g., between 0.02 and 1.0 g/L (e.g., between 0.11 and 5.5 mM)) and culturing cells in a production phase at an osmolality of about 400 to 600 mOsm has been found to increase production of recombinant proteins by animal cell cultures, particularly after an initial culturing at an osmolality of about 280 to 330 mOsm (U.S. Pat. No. 5,856,179; each U.S. patent cited in this document is incorporated by reference in its entirety) and wherein culturing in all phases is also at a selected glutamine concentration (preferably between about 0.2 to about 2 mM; U.S. Pat. No. 6,180,401).

Some of this increase in recombinant protein production may result from a reduction in lactate production that occurs when glucose concentrations in culture media are maintained at low levels. Lactate is known to be a strong inhibitor of cell growth and protein production, and maintaining low glucose concentrations in culture media can result in low levels of lactate production (Glacken et al. (1986) *Biotechnol. Bioeng.* 28:1376-89; Kurokawa et al. (1994) *Biotechnol. Bioeng.* 44:95-103; U.S. Pat. No. 6,156,570). Consequently, depending on other culture conditions, maintaining glucose concentrations at low levels relative to cell concentration is one factor that can contribute to lower levels of lactate production, and thus to higher cell concentrations and increased production of recombinant proteins in animal cell cultures.

When cells are exposed to low glucose concentration in a medium, their metabolism is altered such that both glucose uptake rate and lactate production rate are lower as compared to cells maintained in fed-batch processes having media with high glucose levels at the start of the process (U.S. Pat. No. 6,156,570). Furthermore, the duration of the fed-batch culture can be extended. Consequently, both cell growth rate and protein production rate can be maintained for a longer period as compared to control fed-batch cultures in which cells are grown in media conducive to high levels of lactate production (e.g., media containing high glucose levels at the start of the culture period).

One way to control lactate production by cultured cells to low levels is through an invariant, constant-rate feeding of glucose in a fed-batch process (Ljunggren and Häggström (1994) *Biotechnol. Bioeng.* 44:808-18; Häggström et al. (1996) *Annals N.Y. Acad. Sci.* 782:40-52). Although this invariant, constant-rate feeding of glucose in a fed-batch process can help control lactic acid production by cultured cells to low levels, maximum cell concentrations, growth rates, cell viability levels, and protein production rates are not achieved, because this method of providing glucose typically results in glucose starvation as cell concentrations increase.

Another way to control lactate production by cultured cells to low levels is through the use of glucose delivery systems that rely on sampling cultures at regular intervals. Samples are taken from a culture at regular intervals, and, after the glucose concentration in samples is determined (e.g., through flow injection analysis, as by Male et al. (1997) *Biotechnol. Bioeng.* 55:497-504, or Siegwart et al. (1999) *Biotechnol. Prog.* 15:608-16; or through high pressure liquid chromatography, as by Kurokawa et al. (1994) *Biotechnol. Bioeng.* 44:95-103), measured amounts of glucose are added to the cultures in order to maintain glucose concentrations in media at a sustained low level relative to cell concentration. However, cells may adapt to low glucose concentration by, for example, increasing their ability to take in glucose, and thus produce excessive amounts of lactic acid despite the low glucose concentration.

Furthermore, the risk of microorganism contamination through such sampling-based feedback control methods is significant. Consequently, it is not surprising that the use of these methods for the commercial production of recombinant proteins in animal cell cultures has not proved feasible. The sampling-based feedback control methods for maintaining low levels of glucose concentration in cell culture media have been limited to research uses from the time the early article on such methods was published (Glacken et al., supra); the paper reports that glucose concentrations in culture media were determined by using an on-line autoanalyzer, wherein a glucose-containing sample was mixed with o-toluidine, and a colorimeter, through which the absorbance at 660 nm of the mixture was measured to determine glucose concentration.

For the foregoing reasons there is a need for alternative methods of controlling lactate production by cultured cells to low levels in culture media.

SUMMARY OF THE INVENTION

The present invention provides methods for the restricted feeding of glucose to or into animal cell cultures in fed-batch processes. In association with this restricted feeding, lactate production by cultured cells can be controlled to low levels without requiring the constant-rate feeding of glucose. In some embodiments, lactate production by cultured cells can be controlled to low levels without requiring the sampling of cultures at regular intervals for the determination of glucose concentration in a feedback control method. In particular, the present invention provides a solution to a long-felt need for a method of flexibly controlling lactate production by cultured cells to low levels in order to promote increased production of recombinant proteins in animal cell cultures, especially for commercial-scale production.

The present invention relates to a method of culturing animal cells under conditions wherein glucose is fed into cell cultures in a restricted manner (i.e., restricted feeding), which results in low levels of lactate being produced by cultured cells. This restricted or slow feeding is accomplished through continuous or intermittent feeding of glucose into the cell culture at rates that are less than (i.e., a function of) expected or premodeled rates of glucose consumption by animal cells exposed to a medium containing a high level of glucose. In particular, the invention relates to a method of increasing protein production in animal cell cultures by controlling lactate production to low levels through the restricted feeding of glucose.

Though some embodiments of the invention may employ sampling-based feedback control, other embodiments of the invention do not require sampling-based feedback control. For example, estimates of expected capacities for rates of glucose consumption by cultured animal cells may be augmented by cell concentration measurements, which in some embodiments are made without sampling (e.g., made photometrically). On the basis of cell concentration measurements, glucose delivery rates to cell cultures may be calculated (in real time, if desired) for restricted feeding of glucose to cell cultures, i.e., at a rate less than 100% of an expected or a premodeled rate of glucose consumption by animal cells in a corresponding culture with very similar culture conditions but wherein the glucose concentration, rather than being at a restricted level, is such that any increase in concentration therefrom will not affect the rate of glucose consumption by the cells. As demonstrated in embodiments of the invention, restricted feeding of glucose allows lactic acid production by cultured cells to be controlled to low levels.

In some embodiments of the invention, pH monitoring is included as a supplementary method for estimating lactate consumption and protecting against glucose starvation of cultured cells. The monitoring of pH takes advantage of the fact that cells will consume lactate from the culture if glucose is not available. A rise in culture pH occurs as the cells consume lactate, thus a rise in pH can signal that glucose is not available in the cell culture (i.e., that the cells are starving for glucose). Consequently, in some embodiments of the invention, a feeding strategy that provides a bolus of glucose feed and/or increases the glucose restricted-feed rate to a cell culture upon a rise in pH can protect cells from starving for want of glucose. In some embodiments, the pH measurements are taken without "sampling" (e.g., the pH measurements are made through the in situ use of a pH sensor for which no cell-containing aliquots are withdrawn from the culture in order to measure pH).

In particular, one aspect the invention provides a cell culture method for controlling lactic acid production to low levels in a fed-batch cell culture comprising: mixing animal cells and a medium to form a cell culture; and feeding glucose in a restricted manner into the cell culture. In embodiments of this aspect, the restricted feeding of glucose occurs when glucose is provided at a rate that is a function of an expected rate of glucose consumption by the animal cells when exposed to a medium containing a high level of glucose. In related embodiments of this aspect, the function is multiplication by a percentage less than 100%, including, but not limited to, percentages such as at least 33%, or no more than 45%, of an expected rate. In further related embodiments of this aspect, the restricted feeding of glucose into the cell culture is accomplished without feedback control sampling during culture.

In some embodiments of this aspect of the invention, a cell-concentration sensor is used to monitor cell concentration in the cell culture, and a cell-concentration-sensor-derived measurement is additionally used in calculating the rate at which glucose will be fed in a restricted manner into the cell culture. In other embodiments of this aspect, a pH sensor is used to monitor pH of the cell culture, and, in response to a rise in pH above a predetermined value (e.g., approximately 7), glucose is added to the cell culture (e.g., in a bolus of glucose feed and/or at a new rate of feeding glucose in a restricted manner that is greater than an immediately prior rate of glucose addition; in some embodiments, a new rate may be at least 15%, or no more than 50%, greater than an immediately prior rate, provided that such new rate does not reach or exceed 100% of the expected rate of glucose consumption by control cells exposed to a high level of glucose). In other embodiments, a cell-concentration-sensor-based system may be used in conjunction with a pH-sensor-based system in determining the rate of feeding glucose in a restricted manner into the cell culture. Either the cell-concentration-sensor-based system or the pH-sensor-based system or both may be used without "sampling" of the cell culture.

Another aspect the invention provides a cell culture method for controlling lactic acid production to low levels in a fed-batch cell culture comprising: (a) mixing animal cells and a medium containing a high level of glucose to form a first cell culture; (b) determining a glucose consumption rate (i.e., a premodeled rate) for the animal cells cultured in the first cell culture; (c) mixing animal cells and a medium to form a second cell culture; and (d) feeding glucose in a restricted manner into the second cell culture at a rate that is a function of the determined glucose consumption rate of step (b) (i.e., a function of the premodeled rate of glucose consumption). In related embodiments of this aspect, the function is multiplication by a percentage less than 100%, such as at least 33%, or no more than 45%, of the determined glucose consumption rate (i.e., the premodeled rate). In further related embodiments of this aspect, the restricted feeding of glucose into the second cell culture is accomplished without feedback control sampling of the second cell culture.

In some embodiments of this aspect of the invention, a cell-concentration sensor is used to monitor cell concentration in the second cell culture, wherein a cell-concentration-sensor-derived measurement is additionally used in calculating the rate of feeding glucose in a restricted manner into the second cell culture. In other embodiments of this aspect, a pH sensor is used to monitor pH of the second cell culture, and, in response to a rise in pH above a predetermined value (e.g., approximately 7), glucose is added to the second cell culture (e.g., in a bolus of glucose feed and/or at a new rate of feeding glucose in a restricted manner that is greater than an immediately prior rate of glucose addition; in some embodiments, a new rate may be at least 15%, or no more than 50%, greater than an immediately prior rate). In other embodiments, a cell-concentration-sensor-based system may be used in conjunction with a pH-sensor-based system in determining the rate of feeding glucose in a restricted manner into the second cell culture. Either the cell-concentration-sensor-based system or the pH-sensor-based system or both may be used without "sampling" of the second cell culture.

In methods of the invention, cells are adapted to growth under culture conditions wherein glucose is added to test cell cultures at rates that are restricted in comparison to glucose consumption rates under control culture conditions (e.g., wherein the glucose concentration is such that any increase in concentration will not affect the rate of glucose consumption by the animal cells). In particular, cells from two exemplified restricted-feed cell cultures (differing in the rates at which glucose was fed in a restricted manner into the cultures) produced lower levels of lactate than control cell cultures produced. They also displayed different growth rates and rates of recombinant protein production. "Low-ramp" restricted-feed cultures displayed lower levels of lactate production than the "high-ramp" restricted-feed cultures. "Low-ramp" restricted-feed cultures also displayed higher growth rates and higher rates of recombinant protein production than "high-ramp" restricted-feed cultures. In general, both the low-ramp restricted-feed cultures and the high-ramp restricted-feed cultures displayed lower lactate production rates, higher growth rates, and higher rates of recombinant protein production than control cultures.

Other features and advantages of the invention will be apparent from the following description of preferred embodiments thereof, and from the claims.

BRIEF DESCRIPTION OF THE DRAWINGS

FIG. 8. BMP-2 Titer (Normalized): Control vs. Premodeled Feeds

FIG. 9. Glucose & Lactate Concentrations: Control vs. Premodeled Feeds.

DETAILED DESCRIPTION OF THE INVENTION

Definitions: The phrase "animal cells" encompasses invertebrate, nonmammalian vertebrate (e.g., avian, reptile and amphibian), and mammalian cells. Nonlimiting examples of invertebrate cells include the following insect cells: *Spodoptera frugiperda* (caterpillar), *Aedes aegypti* (mosquito), *Aedes albopictus* (mosquito), *Drosophila melanogaster* (fruitfly), and *Bombyx mori* (silkworm/silk moth). Preferred mammalian cells include baby hamster kidney (BHK), Chinese hamster ovary (CHO), human kidney (293), normal fetal rhesus diploid (FRhL-2), and murine myeloma (e.g., SP2/0 and NS0) cells.

The phrase "base inoculation medium" refers to a solution or substance containing nutrients, but not glucose, in which a culture of cells is initiated. "Base feed medium" contains the same nutrients as the base inoculation medium, but is a solution or substance with which the culture of cells is fed after initiation of the culture.

A "batch culture" refers to a culture of cells whereby the cells receive base inoculation medium containing glucose at the initiation of the culture, and whereby the cell culture delivers product, e.g., recombinant protein, only at termination of the culture. Similarly, a "fed batch culture" of cells delivers product only at its point of termination. However, cells in a fed batch culture receive base inoculation medium containing glucose at the initiation of the culture and are fed base feed medium containing glucose at a one or more points after initiation, but before termination.

"High level of glucose" means a glucose concentration in animal cell cultures whereby any increase in the glucose concentration will not affect the glucose consumption rate of the cells.

Figure 1:
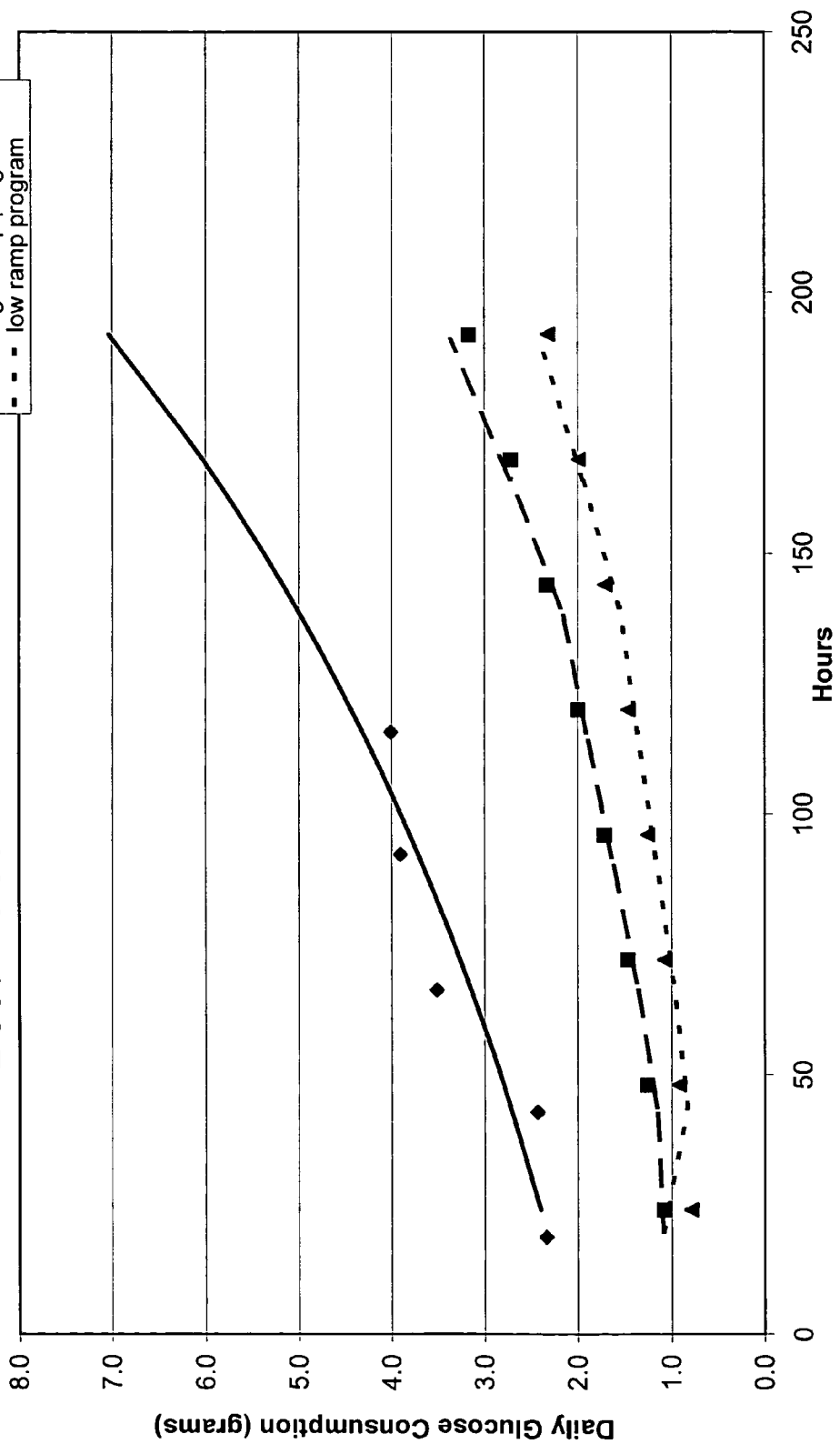
FIG. 1. Control vs. Restricted Glucose Feeds: Best-Fit Curve

A "glucose consumption rate" reflects glucose consumption by animal cells in culture at a point in time. Glucose consumption rates may be represented graphically (as in the upper "best-fit" curve of FIG. 1) or through a mathematical function (as in the legend of FIG. 1).

"Feeding glucose in a restricted manner" and/or "restricted feeding of glucose" and/or "glucose is fed in a restricted manner" and/or similar phrases refer to providing a restricted amount of glucose to a culture such that the restricted amount provided is determined or calculated by a function, and is less than 100% of the amount of glucose expected or determined to be consumed by a control culture. A "control culture" means a culture of the same animals cells under similar culture conditions (e.g., a culture of the same cells in the similar base inoculation and feed media, at the same temperature, starting with the same initial cell concentration, etc.) except that the culture has a high level of glucose. Thus, the function by which the restricted amount of glucose provided can be determined or calculated may be a function of an expected rate of glucose consumption, or a function of a determined glucose consumption rate, by cells in a control culture. Feeding glucose in a restricted manner may occur whereby glucose is provided at a certain concentration or concentrations over a period of time, i.e., at a certain rate or rates, and/or whereby glucose is provided by one or more boluses of glucose feed.

The phrases "function of an expected rate of glucose consumption" or "function of a determined glucose consumption rate" (where the determined glucose consumption rate is a premodeled rate) may include a number of mathematical relationships between an expected or a premodeled rate of glucose consumption and a glucose restricted-feed rate (or restricted rate of glucose addition), including relationships wherein glucose feed rate is the product of (i.e., the result of multiplication of) (1) an expected or a premodeled rate of glucose consumption at a point in time during the duration of cell culture and (2) a percentage value less than 100%. Quadratic, cubic, and exponential functions are also among the many mathematical relationships encompassed by the invention. However, applicable functions within the scope of the invention do not include those wherein the glucose restricted-feed rate is an invariant, constant-rate addition over the duration of cell culture.

"Low level of lactic acid" (or "low level of lactate") in a cell culture refers to a lactic acid (or lactate) concentration that is lower than the lactic acid (or lactate) concentrations found in cells cultured with a high level of glucose.

"Sampling" includes withdrawing cell-containing samples from animal cell cultures (e.g., in a bioreactor) for purposes of measuring characteristics of the culture medium. "Sampling" does not include measurements of cell concentration wherein no cell-containing samples or aliquots are removed or separated from the culture for purposes of measuring cell concentration. For example, photometric-based estimations of cell concentration may be accomplished without "sampling" a culture maintained in a transparent or translucent container.

In addition, "sampling" does not include in situ use of a pH sensor to measure the pH of a medium in which animal cells are cultured wherein no cell-containing samples or aliquots are removed from the culture for purposes of measuring pH. The use of a probe to measure the pH of a cell culture medium is not "sampling" as herein defined if no cell-containing samples or aliquots are removed or separated from the culture.

Following long-standing convention, the terms "a" and "an" mean "one or more" when used in this application, including the claims. Even though the invention has been described with a certain degree of particularity, it is evident that many alternatives, modifications, and variations will be apparent to those skilled in the art in light of the disclosure. Accordingly, it is intended that all such alternatives, modifications, and variations, which fall within the spirit and scope of the invention, be embraced by the defined claims.

The present invention relates to methods of culturing animal cells such that cultures maintain low levels of lactic acid, result in increased cell viability for a longer period of time, and produce increased levels of recombinant protein. One of skill in the art will recognize that the methods disclosed herein may be used to culture many of the well-known animal cells routinely used and cultured in the art, i.e., the methods disclosed herein are not limited to use with only the animal cells listed within the definition of animal cells.

The methods of the invention relate to feeding glucose in a restricted manner to a culture of animal cells. As further detailed in Example 2, feeding glucose in a restricted manner may occur by providing glucose at a rate that is a function of an expected or determined consumption rate of glucose (e.g., a premodeled rate of glucose consumption) by animal cells in a control culture, e.g., cells cultured with a high level of glucose. Feeding glucose in a restricted manner may also include providing one or more boluses of glucose.

The conditions of the control culture may be determined by one of skill in the art without undue experimentation. For example, one of skill in the art understands that animal cells are typically cultured in a "medium", which generally refers to a solution comprising nutrients including glucose. As such, a skilled artisan will know that glucose should be added to the base inoculation and feed media prior to inoculation and feeding of the animal cells, respectively. It will be recognized that the amount of glucose added to the base inoculation medium and base feed medium may differ. Additionally, one of skill in the art will recognize which medium is appropriate to culture a particular animal cell (e.g., CHO cells), and the amount of glucose that the medium should contain to generate animal cell cultures such that there is a high level of glucose (see, e.g., Mather, J. P., et al. (1999) "Culture media, animal cells, large scale production." Encyclopedia of Bioprocess Technology: Fermentation, Biocatalysis, and Bioseparation. Vol. 2: 777-785). In other words, one of skill in the art will recognize the glucose concentration at which a particular cell must be cultured such that any increase in the glucose concentration of the culture will not affect the glucose consumption rate of the cell. A high level of glucose in a cell culture is to be distinguished from a high level of glucose added to base inoculation and feed media; glucose concentration in the latter (e.g., at 44, 200, or 280 g/L) is typically diluted upon addition to a cell culture.

One of skill in the art will additionally recognize that the optimum concentration of other nutrients (e.g., glutamine, iron, Trace D elements), or agents designed to control for other culture variables (e.g., the amount of foaming and osmolality) will vary depending on the animal cell. As such, adjustment of the concentrations of such nutrients or agents in the base inoculation and feed media are routine in the art. Furthermore, a skilled artisan will recognize at what temperature and concentration a particular cell should be cultured.

In some embodiments of the invention, the cell concentration, and/or pH of the culture is monitored and used in calculating the rate of restricted feeding of glucose. Methods of measuring cell concentration and/or pH of a culture are well known in the art; such methods include, but are not limited to, using a Cedex (Innovatis GmbH, Bielefeld, Germany) and/or a CASY (Scharfe system GmbH, Reutlingen, Germany) instrument to determine cell concentration, and/or a pH sensor. Particularly useful for the claimed invention are methods of determining the cell concentration and pH that do not require sampling, i.e., withdrawing cell-containing samples from the animal culture, including, but not limited to, use of a capacitance probe, optical density probe and/or a turbidity probe to measure cell concentration, and/or a potentiometric probe or pH sensitive dyes to measure pH.

In some embodiments of the invention, a cell-concentration-derived measurement, and/or a pH-sensor-derived measurement, determines that feeding glucose in a restricted manner should subsequently continue at a new rate that is greater than an immediately prior rate. One of skill in the art will recognize that the new rate at which glucose is fed in a restricted manner should still be less than 100% of an expected or determined glucose consumption rate. Thus, where the immediately prior rate is, e.g., 99% of an expected or determine glucose consumption rate, the new rate should not increase by more than 1% of the immediately prior rate. In other embodiments, the new rate is increased by 1-15% of the immediately prior rate. In some embodiments of the invention, the new rate is increased by at least 15% of the immediately prior rate. In other embodiments of the invention, the new rate is increased by not more than 50% of the immediately prior rate.

EXAMPLES

Example 1

Media

Example 1.1

Inoculation Media

Base inoculation medium was formulated to include the same components as DMEM/F12 Medium, but with the following components being added: 200 mg/L dextran sulfate (U.S. Pat. No. 5,318,898 describes use of dextran sulfate in culture media), 10 mg/L Nucellin (a human insulin analog of recombinant DNA origin; Eli Lilly (Indianapolis, Ind.)), and 2.4 g/L polyvinyl alcohol (PVA). The base inoculation medium made for these experiments lacked glucose. For control inoculation medium, approximately 10 g/L glucose was added to the base inoculation medium prior to inoculation. For the inoculation medium used in glucose restricted-feed cultures, approximately 0.8 g/L glucose and 1.3 g/L NaCl were added to the base inoculation medium; the NaCl was added so that the starting osmolality of the inoculation medium used in glucose restricted-feed cultures was similar to the starting osmolality of the control inoculation medium.

Example 1.2

Feed Media

Base feed medium was formulated to consist of the same components as DMEM/F12 Medium-base inoculation medium; the base feed medium formulated for these experiments lacked glucose. For control feed medium, about 44 g/L glucose was added to the base feed medium.

Example 2

Setting Glucose Addition Rates

One approach to setting glucose addition rates for restricted-glucose feed cultures involved examining glucose consumption rates by CHO cells throughout a typical control fed-batch culture. Glucose concentration in a typical control culture began at a high level (e.g., about 10 g/L) and diminished steadily during normal exponential growth; glucose additions were made after Day 3. For these control cultures, glucose supplementation is needed to prevent glucose depletion (e.g., see glucose concentration profile for control culture in FIG. 9).

Glucose concentrations were determined for control cultures using sampling-based methods, wherein samples were taken at various points in time after inoculation, and the glucose concentrations of samples were determined. Samples were taken daily and were analyzed using the Bioprofile 100 Analyzer (Nova Biomedical Corp., Waltham, Mass.), which measures concentrations of glucose, lactate, glutamine, glutamate, and ammonium. The glucose concentrations of some samples were also estimated using a Glucose HK kit (Sigma-Aldrich Co., St. Louis, Mo.; Cat. No. GAHK-20).

In this sampling-based approach, the rate of glucose consumed during the exponential growth phase from the media of control cultures was plotted versus time over increments of hours and days. An exponential best-fit curve (i.e., $y = a \cdot e^{bx}$) was then generated using these data points (for the best-fit curve of FIG. 1, for example, a=2.058 and b=0.0064). From this curve, rates of glucose consumption (g/L/hr) were extrapolated to provide low-ramp and high-ramp restricted-glucose feed amounts at any given time point. For the low-ramp restricted-feed cultures, values of the control best-fit curve plot were multiplied by 33% to estimate rates at which glucose would be supplied to the low-ramp restricted-feed cultures (see "low ramp" solid triangles of FIG. 1). Similarly, values of the control best-fit curve plot were multiplied by 45% to estimate rates at which glucose would be supplied to the high-ramp restricted-feed cultures (see "high ramp" solid squares of FIG. 1). The multipliers 33% and 45% were chosen arbitrarily. All multipliers having percentages less than 100%, or functions relating restricted glucose feed rate to an expected or a premodeled rate of glucose consumption wherein a calculated restricted glucose feed rate is less than an expected or a premodeled rate of glucose consumption, are within the scope of the invention (except that permissible functions do not include those relationships wherein the resulting rate of glucose addition is an invariant, constant-rate addition over the duration of cell culture).

Another approach to feeding glucose in a restricted manner involved utilizing a pH-controlled response system in a programmed restricted-glucose feed culture system. When a culture of mammalian cells (such as CHO cells) is depleted of glucose, the cultured cells begin consuming lactate as an alternate carbohydrate energy source. The decrease in lactate concentration in the cell culture results in a rise in pH (to which the pH-controlled response system reacts).

In implementing this approach, a syringe pump of a glucose solution was programmed to deliver glucose at a restricted rate (e.g., 0.032 g/L/hr; see initial "low ramp" addition rate of Table 2) except that, when the pH of the culture medium rose by 0.02 pH units above a predetermined value of 7.00, delivery of a bolus of glucose feed (0.05 to 0.2 g glucose delivered from feed media per liter culture) was triggered, and, in addition, the restricted delivery rate by the syringe pump was subsequently increased to a level 15% to 50% higher than the previous restricted-delivery rate. For example, delivery of a bolus of 0.25 to 1.0 mL feed medium containing 0.2 g/mL glucose provides to a 1 L cell culture approximately 0.05 to 0.2 g glucose.

In another approach, cell concentration of a cell culture is measured without sampling in order to assist in calculating rates for restricted feeding of glucose. In initiating tests of this approach, glucose was fed into the culture so that the concentration of glucose remained at a level considered to be adequate for the cell concentration in the culture. A Wedgewood spectrophotometer (653 Absorbance Monitor with Model BT65 Series Insertion Sensor, Wedgewood Technology Inc., San Carlos, Calif.) was used to estimate cell concentration in cultures in real time. A laser turbidity probe (e.g., Model LA-300LT, ASR Co., Ltd., Tokyo) alternatively may be used to estimate cell concentration. A laser beam from the laser turbidity probe is emitted through the cell culture from the probe light source, and a calibration curve is used to convert optical density values into cell concentrations. Although light absorption properties of cells are not constant and the size distribution of cells changes during cultivation, Zhou and Hu ((1994) *Biotechnol. Bioeng.* 44:170-77) found total cell concentration of a mouse-mouse hybridoma cell line, MAK, correlated linearly to signal from a laser turbidity probe at cell concentrations below $3.0 \times 10^9$ cells/liter. Consequently, spectrophotometric measurements of cell concentration may be accomplished (without sampling) in order to assist in calculating rates for restricted feeding of glucose.

Another approach combines a pH-sensor-based response system and a cell-concentration-derived system with the use of a feed ramp-up program (set to approximate the expected glucose demands of a cell culture over time). Either the pH-sensor-based response system or the cell-concentration-derived system or both may be used without sampling of the cell culture.

Use of a glucose sensor probe to measure glucose concentration directly (and not simply as reflected in pH or cell concentration measurements) in real time (and in a way that does not require the sampling of a culture) is not required to practice the invention, particularly because the invention provides restricted rates of glucose delivery to animal cell cultures, rather than simply maintaining a low glucose concentration in the culture, to overcome the ability of cells to adapt to a low glucose concentration. However, use of a glucose sensor in practicing the disclosed methods may be within the scope of the present invention.

Example 3

Production of BMP-2 in CHO Cells

The purpose of these experiments was to implement restricted-glucose feeding strategies in order to control lactate production to low levels in fed-batch cell cultures (specifically one liter (1 L) cultures) that used CHO cells (specifically EMCG5 cells) for production of recombinant bone morphogenetic protein-2 (BMP-2) (U.S. Pat. Nos. 5,318,898; 5,618,924; and 5,631,142 further describe BMP-2 proteins and their production). The effects of the restricted-glucose feeding strategies on cell concentration and viability, lactate production, protein productivity, and extended batch duration, were monitored.

Sterile glucose solution was fed in a restricted manner into the bioreactor using a syringe pump programmed to increase the glucose provided throughout the fed-batch cell culture. In one set of tests, glucose was added to the culture as a function of (e.g., as a percentage of) a previously determined rate of glucose consumption by the animal cells when exposed to a high level of glucose (i.e., as a function of a premodeled rate).

Glucose starvation incidents were also monitored using a pH sensor (Bradley-James Corp.) that did not require sampling. Accordingly, a rise in pH 0.02 units above a predetermined value of 7.00 was taken to indicate that glucose had been completely depleted from the culture media and that cells had begun to consume lactic acid. The decrease in lactic acid levels in cultures causes an increase in the pH of cell culture media; this relationship allows for a pH-sensor-based system for anticipating glucose starvation incidents.

In order to evaluate a pH-sensor-based system for effectiveness in preventing glucose starvation in restricted-glucose feed experiments, a syringe pump was programmed to deliver a bolus of glucose feed into the bioreactor if pH rose above a predetermined value of 7.00. A rise in pH 0.02 units above 7.00 triggered a bolus of glucose feed to be delivered, with the subsequent restricted rate of continuous glucose delivery being increased by 15% in some tests, and by 50% in others.

In these experiments, Applikon® 2 L bioreactors with 1 L working volume (Applikon Biotechnology, Foster City, Calif.) were used. Air sparge was provided on-demand to maintain dissolved oxygen at 23% of air saturation, and Medical Grade antifoam C emulsion (Dow Corning Corporation, Midland, Mich.) was used to prevent foaming. Temperature was maintained at 37° C. throughout the fed-batch culturing. Becton Dickinson® syringes (Becton, Dickinson and Company, Franklin Lakes, N.J.) were filled aseptically with control or experimental glucose solution to deliver glucose to control or restricted-feed cultures, respectively, in the bioreactors.

In a first experiment (i.e., an expected increase feed experiment), a representative control culture used increasing amounts of glucose each day, and an exponential best fit curve was used to approximate the amount of glucose consumed by the control culture each day. Using the best fit curve as a basis, a syringe pump (Yale Apparatus, Wantagh, N.Y.) was set to feed glucose to the experimental culture at a restricted-feed rate, i.e., approximately 50-70% of the amount consumed by the control culture. Each day, the restricted-feed rate was changed to account for increasing cell density. The concentration of the glucose feed was 200 g/L.

Figure 2:
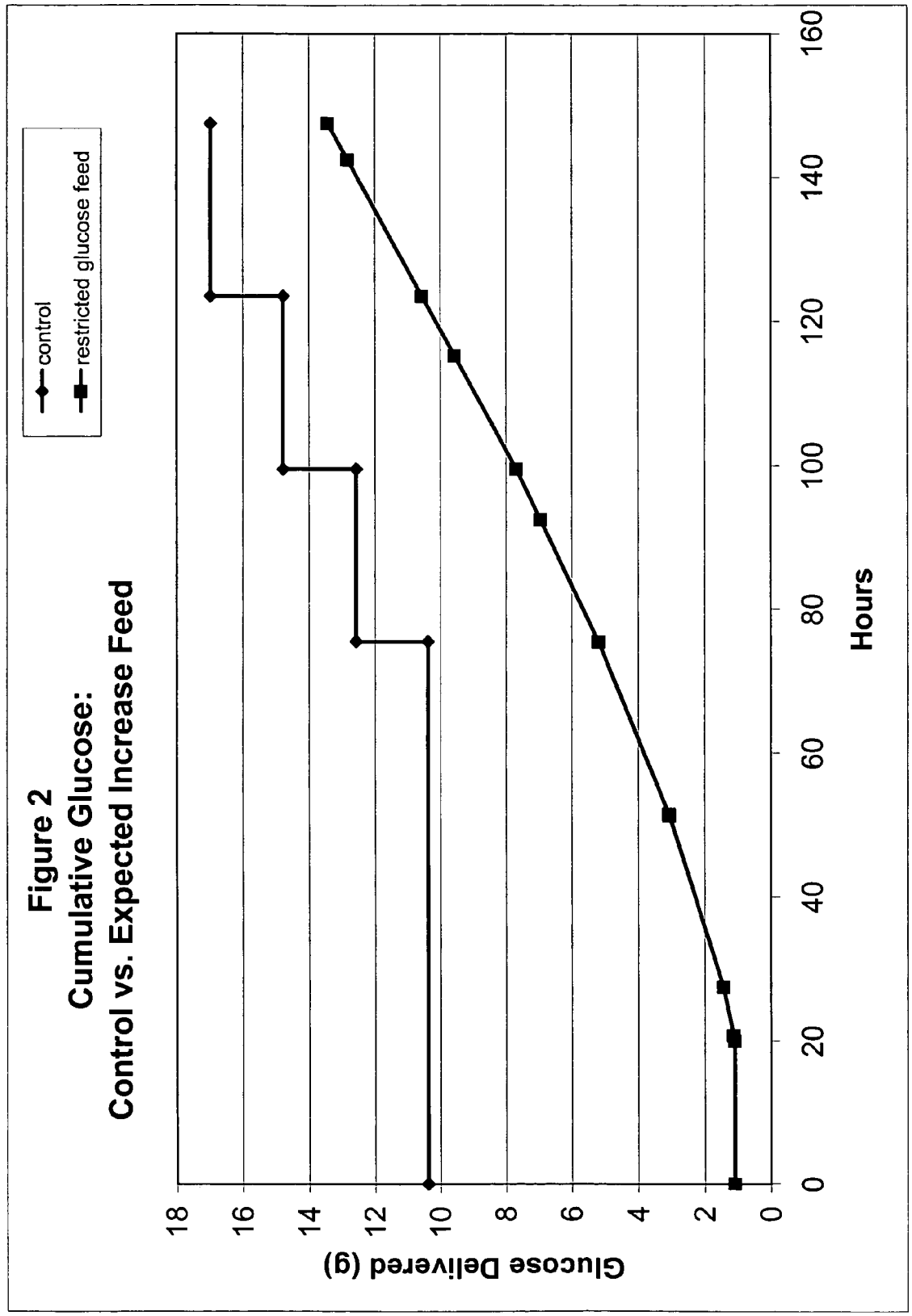
FIG. 2. Cumulative Glucose: Control vs. Expected Increase Feed

The initial glucose concentration in the control culture (1 L) was 10.38 g/L. After slightly more than three days, glucose (2.2 g) was added at 24 hr intervals to the control culture (i.e., at 75.5, 99.5, and 123.5 hrs of culture) (Table 1; FIG. 2; and FIG. 6). The initial glucose concentration in the restricted-feed culture (1 L) was 1.1 g/L. The rate of continuous restricted feeding of glucose into the restricted-feed culture was increased four times (after 27.5, 51.5 75.5, and 99.5 hrs of culture) from an initial continuous restricted feeding rate of 0.046 g/L/hr (which was maintained in the 20-to-27.5 hr culture period) (Table 1).

TABLE 1

Expected Increase Feed Experiment: Glucose Addition

| Glucose Addition to 1 L Control Culture (initial glucose concentration: 10.38 g/L) | | Addition Rates to Restricted-Feed Culture (initial glucose concentration: 1.1 g/L) | |
| --- | --- | --- | --- |
| Point (hrs) | Amount (g) | Period (hrs) | Rate (g/L/hr) |
| — | — | 0-20 | 0 |
| — | — | 20-27.5 | 0.046 |
| — | — | 27.5-51.5 | 0.068 |
| 75.5 | 2.2 | 51.5-75.5 | 0.088 |
| 99.5 | 2.2 | 75.5-99.5 | 0.104 |
| 123.5 | 2.2 | 99.5-147.5 | 0.12 |

Figure 6:
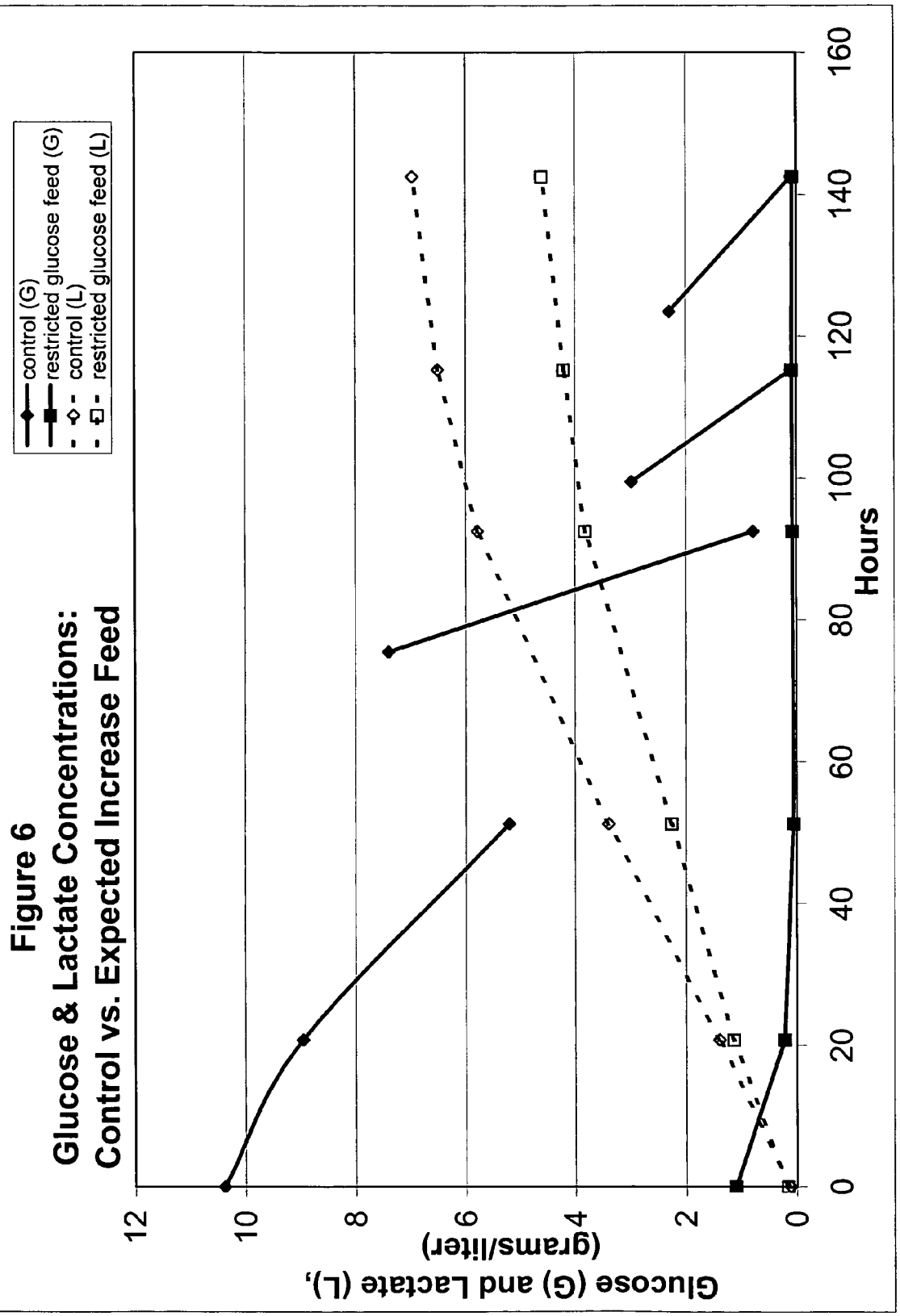
FIG. 6. Glucose & Lactate Concentrations: Control vs. Expected Increase Feed

The rate of glucose consumption in the restricted-feed culture approximated the restricted rate of glucose delivery throughout the duration of the continuous restricted feeding of glucose into the restricted-feed culture. This is evidenced by the glucose concentration in the restricted-feed culture remaining near zero after continuous feeding of glucose in a restricted manner began after 20 hrs of culture (FIG. 6). Glucose consumption rates in the control cultures, on the other hand, were not limited by a restricted rate of glucose delivery. Consequently, glucose consumption rates in the control cultures continued for several days at higher levels than in the restricted-feed cultures (Table 6). Lactate concentrations (FIG. 6) and lactate production rates (Table 7) also remained lower for the restricted-feed cultures than the control cultures throughout this expected increase feed experiment.

In a second experiment (i.e., a premodeled feeds experiment), ramp programming of a dual-syringe pump (KD Scientific, Holliston, Mass.) was utilized. For this premodeled feeds experiment, the glucose concentration was 0.28 g/mL for the high-ramp glucose feed, and 0.20 g/mL for the low-ramp glucose feed. In contrast to the expected increase feed experiment, whereby the syringe pump continuously delivered glucose at a preset restricted-feed rate over a period of time, e.g., 0.046 g/hr from hours 20-20.7 and 0.068 g/hr from hours 27.5 to 51.5, etc., the ramp programming of the syringe pump in the premodeled feeds experiment allowed the restricted-feed rate of glucose to ramp up gradually to resemble 33% and 45% of the exponential best fit curve of glucose consumed by the control culture each day. The ramp programming allowed initial and final restricted rates to be programmed for each time period, e.g., 12 hrs, and the pump would change the rate continuously in a linear fashion during that time period. Table 2 provides representative data on glucose addition for this premodeled feeds experiment.

TABLE 2

Premodeled Feeds Experiment: Glucose Addition

| Glucose Addition to 1 L Control Culture (initial glucose concentration: 8.4 g/L) | | Restricted-Feed | | | |
| --- | --- | --- | --- | --- | --- |
| | | | | Addition Rates to Restricted-Feed Cultures (initial glucose concentration: 0.88 g/L) | |
| | | | Syringe Rate | Low Ramp (0.2 g/mL feed) | High Ramp (0.28 g/mL feed) |
| Point (hrs) | Amount (g) | Period (hrs) | mL/hr | g/hr added to 1 L | g/hr added to 1 L |
| — | — | 0-19.75 | 0 | 0 | 0 |
| — | — | 19.75-43.75 | 0.160-0.184 | 0.0320-0.0368 | 0.0448-0.0515 |
| — | — | 43.75-67.75 | 0.184-0.224 | 0.0368-0.0448 | 0.0515-0.0627 |
| 67.5 | 2.2 | 67.75-91.75 | 0.224-0.264 | 0.0448-0.0528 | 0.0627-0.0739 |
| 94.75 | 2.2 | 91.75-115.75 | 0.264-0.304 | 0.0528-0.0608 | 0.0739-0.0851 |

TABLE 2-continued

Premodeled Feeds Experiment: Glucose Addition

| Glucose Addition to 1 L Control Culture (initial glucose concentration: 8.4 g/L) | | Restricted-Feed | | | |
|---|---|---|---|---|---|
| | | | | Addition Rates to Restricted-Feed Cultures (initial glucose concentration: 0.88 g/L) | |
| | | | Syringe Rate | Low Ramp (0.2 g/mL feed) | High Ramp (0.28 g/mL feed) |
| Point (hrs) | Amount (g) | Period (hrs) | mL/hr | g/hr added to 1 L | g/hr added to 1 L |
| 119.75 | 2.2 | 115.75-139.75 | 0.304-0.344 | 0.0608-0.0688 | 0.0851-0.0963 |
| 143.75 | 2.2 | 139.75-140.25 | 0.344-0.346 | 0.0688-0.0692 | 0.0963-0.0969 |
| 167.75 | 2.2 | 140.25-164.25 | 0.400-0.450 | 0.0800-0.0900 | 0.1120-0.1260 |
| 191 | 2.2 | 164.25-191 | 0.450 | 0.0900 | 0.1260 |

Figure 3:
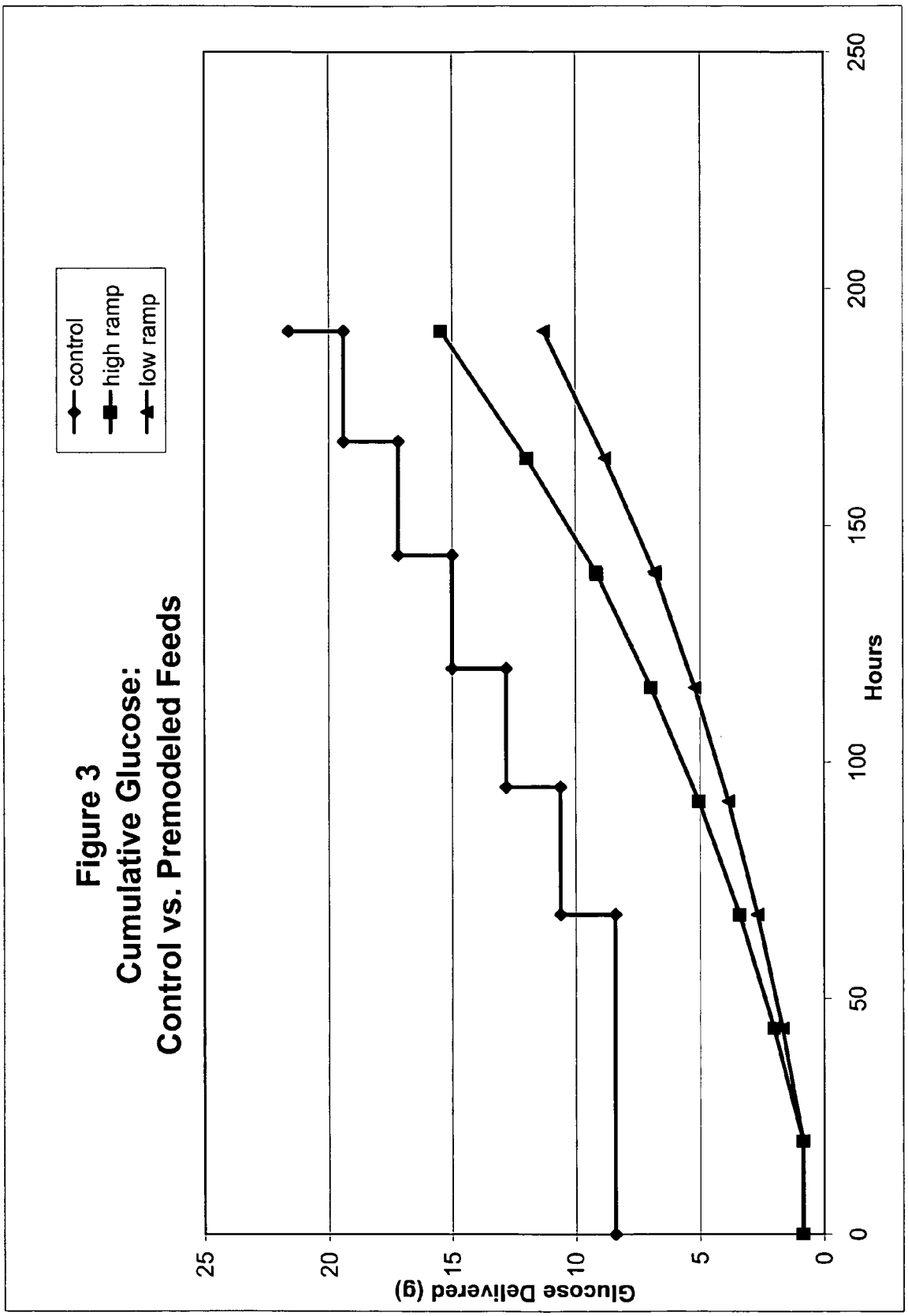
FIG. 3. Cumulative Glucose: Control vs. Premodeled Feeds

FIG. 2 depicts the cumulative amount of glucose delivered over time for the expected increase feed experiment, and FIG. 3 depicts the cumulative amount of glucose delivered over time for the premodeled feeds experiment. FIGS. 2 and 3 each include the initial amounts of glucose provided in both control and restricted-feed reactors (and not simply amounts of total syringe-delivered glucose). In both experiments, a control batch had an initially high level of glucose, and glucose (2.2 g) was added on a daily basis after 72 hrs. For restricted-feed cultures, the bioreactors had on Day 0 about 1 g/l glucose, and syringe delivery of glucose began after about 20 hrs.

Figure 4:
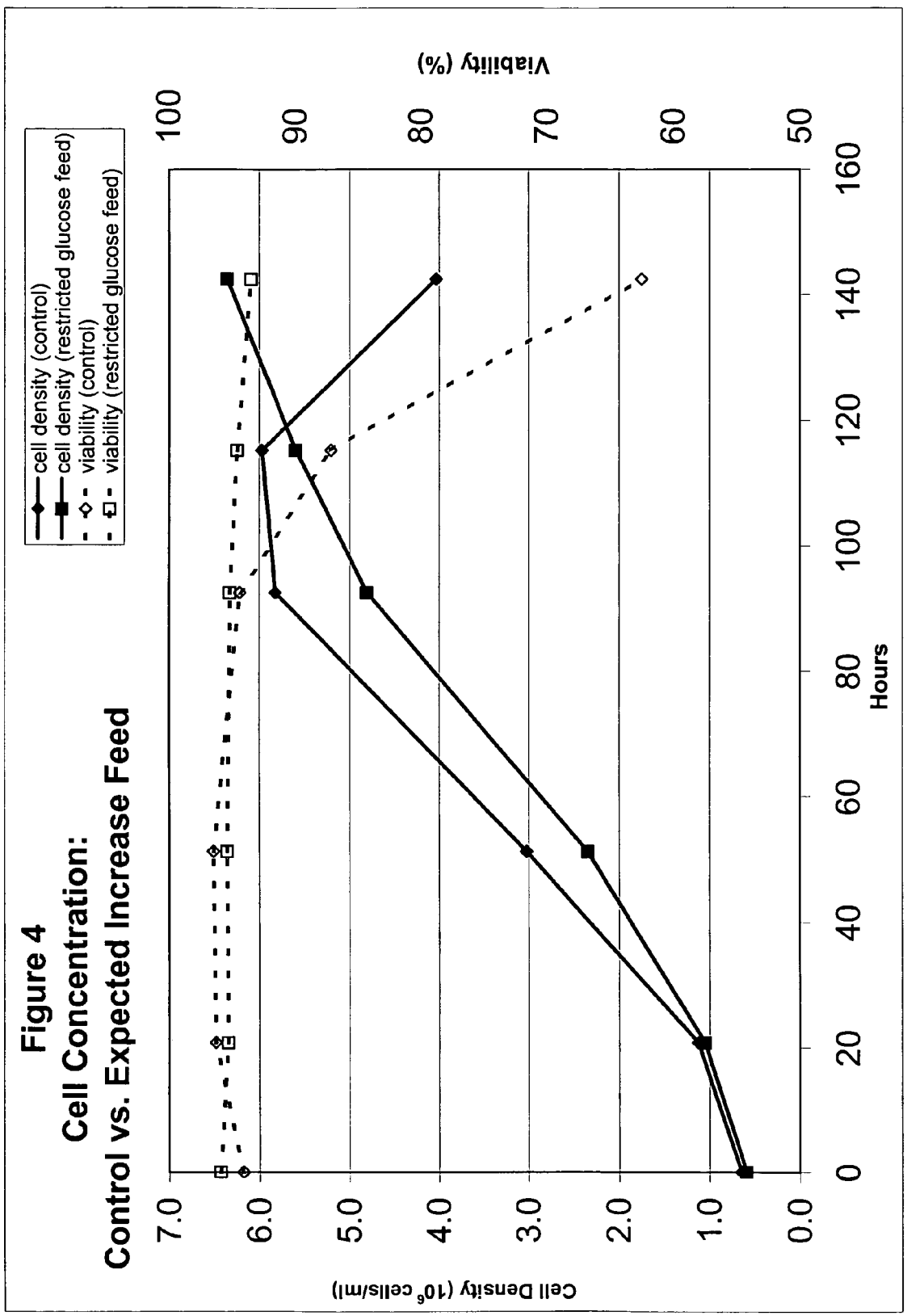
FIG. 4. Cell Concentration: Control vs. Expected Increase Feed

The expected increase feed experiment demonstrated that cell growth in the restricted-feed culture initially lagged compared to cell growth in the control culture, but that cell growth in the restricted-feed culture eventually reached a higher final cell concentration on day 6 (FIG. 4). In the control culture, cell concentration peaked much earlier, and viability began to decline rapidly after Day 4 (FIG. 4). In contrast to the control culture, cell growth rate in the restricted-feed culture remained positive through Day 6 (Table 3).

Although the restricted-feed culture reached a higher final cell concentration compared to control culture by day 6, the cultures had similar concentrations at day 5 (FIG. 4) These data demonstrate that the decreased viability of the cells in the control culture compared to the viability of the cells in the restricted-feed culture was not a function of the cells reaching the maximum capacity of the bioreactor. Instead, the data in FIG. 4, combined with the demonstration of a low level of lactate in the restricted-feed cultures compared to the level of lactate in control cultures (FIG. 6) suggests that the increased viability of cells cultured in the restricted-feed cultures was a function of the low level of lactate achieved by feeding glucose in a restricted manner to the cells.

TABLE 3

Expected Increase Feed Experiment: Cell Growth Rates
(Cedex μ values per hr; Cedex μ values = cell
concentration in units of $10^5$ cells per mL)

| Day | Control Growth Rates ($\mu \cdot (hr^{-1})$) | Restricted-Feed Growth Rates ($\mu \cdot (hr^{-1})$) |
|---|---|---|
| 1 | 0.027 | 0.027 |
| 2 | 0.032 | 0.026 |
| 4 | 0.016 | 0.017 |
| 5 | 0.001 | 0.007 |
| 6 | −0.014 | 0.005 |

Figure 5:
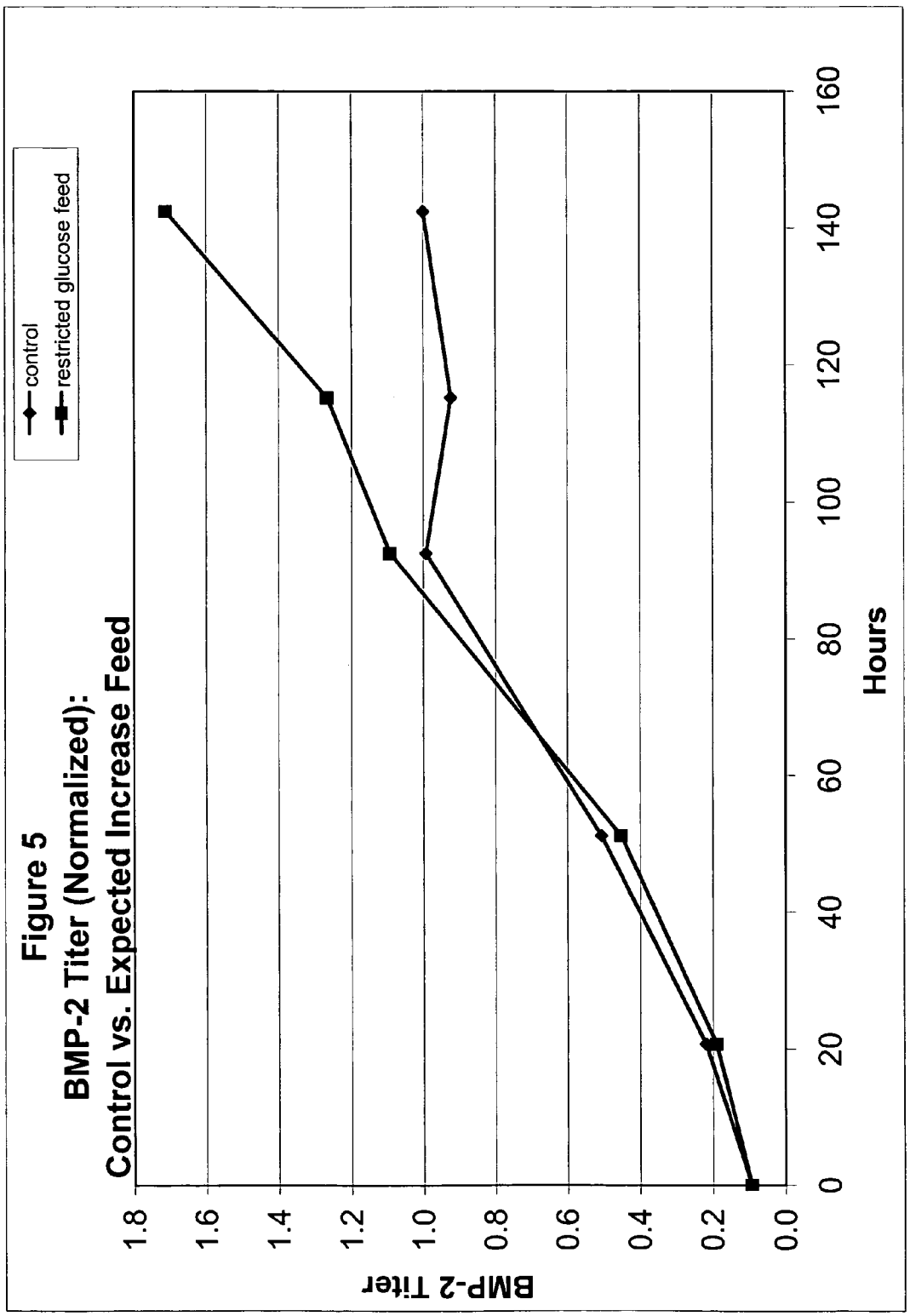
FIG. 5. BMP-2 Titer (Normalized): Control vs. Expected Increase Feed

FIG. 5 presents graphs of the normalized BMP-2 titers. BMP-2 titer values were normalized as a fraction of the BMP-2 titer value on Day 6 of the expected increase feed experiment. Table 4 presents values for corresponding BMP-2 production rates. BMP-2 production rates are normalized as a fraction of the BMP-2 production rate of the control culture on Day 1. After Day 4, BMP-2 titers leveled off for the control culture, but continued to increase for the restricted-feed culture (FIG. 5). In contrast to the control culture, BMP-2 production rates of the restricted-feed culture remained positive through Day 6 (Table 4). It should be noted that although FIG. 5 suggests that control cultures demonstrated a slightly decreased BMP-2 titer on day 5, it is likely that the small decrease seen is a reflection of experimental variability and not of a true decrease in the BMP-2 titer of the culture.

TABLE 4

Expected Increase Feed Experiment:
BMP-2 Production Rate (Normalized)

| Day | Control Production Rate | Restricted-Feed Production Rate |
|---|---|---|
| 1 | 1.00 | 0.84 |
| 2 | 0.71 | 0.77 |
| 4 | 0.40 | 0.65 |
| 5 | −0.07 | 0.21 |
| 6 | 0.08 | 0.40 |

Maintaining a low level of lactic acid using a strategy of feeding glucose in a restricted manner enhanced cell growth and protein productivity. The final titer of BMP-2 was about 70% higher in the restricted-feed culture (FIG. 5), and the BMP-2 production rate did not become negative as it did for the control culture (Table 4).

FIG. 6 presents profiles of glucose concentration (g/L) and lactate concentration (g/L) from the expected increase feed experiment, and Table 5 presents corresponding representative data on glucose concentration (g/L) and lactate concentration (g/L) from this experiment. Table 6 presents values for corresponding glucose consumption rates, and Table 7 presents values for corresponding lactate production rates.

TABLE 5

Expected Increase Feed Experiment:
Glucose and Lactate Concentrations

| Hours | Control | Restricted-Feed |
|---|---|---|
| Glucose Concentration (g/L) | | |
| 0 | 10.38 | 1.10 |
| 20.75 | 8.96 | 0.22 |
| 51.25 | 5.20 | 0.06 |
| 75.5 | 7.40 | — |
| 92.5 | 0.78 | 0.07 |
| 99.5 | 2.98 | — |
| 115.25 | 0.10 | 0.08 |
| 123.5 | 2.30 | — |
| 142.5 | 0.10 | 0.07 |
| Lactate Concentration (g/L) | | |
| 0 | 0.12 | 0.16 |
| 20.75 | 1.40 | 1.14 |
| 51.25 | 3.40 | 2.26 |
| 75.5 | — | — |
| 92.5 | 5.78 | 3.82 |
| 99.5 | — | — |
| 115.25 | 6.50 | 4.20 |
| 123.5 | — | — |
| 142.5 | 6.96 | 4.60 |

TABLE 6

Expected Increase Feed Experiment:
Glucose Consumption Rate

| Day | Control $Q_{glucose}$ (mg/$10^6$ cells/day) | Restricted-Feed $Q_{glucose}$ (mg/$10^6$ cells/day) |
|---|---|---|
| 1 | 1.90 | 1.32 |
| 2 | 1.54 | 1.02 |
| 4 | 0.90 | 0.66 |
| 5 | 0.51 | 0.53 |
| 6 | 0.39 | 0.48 |

TABLE 7

Expected Increase Feed Experiment:
Lactate Production Rate

| Day | Control $Q_{lactate}$ (mg/$10^6$ cells/day) | Restricted-Feed $Q_{lactate}$ (mg/$10^6$ cells/day) |
|---|---|---|
| 1 | 1.71 | 1.41 |
| 2 | 0.82 | 0.55 |
| 4 | 0.32 | 0.26 |
| 5 | 0.13 | 0.08 |
| 6 | 0.08 | 0.06 |

For the restricted-feed culture in the expected increase feed experiment, glucose consumption rates were lower for the restricted-feed culture than the control culture for Day 1 through Day 3 (Table 6), and lactate production rates throughout the culture period were lower for the restricted-feed culture than the control culture (Table 7), which resulted in a lower lactate concentrations for the restricted-feed culture throughout the culture period (FIG. 6).

Osmolality profiles and the amount of titrant (a mixture of sodium carbonate and sodium bicarbonate) used per day in each of the bioreactors were also measured. Table 8 presents osmolality profiles, and Table 9 presents the amount of titrant used per day (per 1 L working volume), under each of the two culture conditions.

TABLE 8

Expected Increase Feed Experiment: Osmolality

| Day | Control Osmolality (mOsm/L) | Restricted Glucose Osmolality (mOsm/L) |
|---|---|---|
| 0 | 286 | 289 |
| 1 | 295 | 312 |
| 2 | 340 | 324 |
| 4 | 382 | 371 |
| 5 | 394 | 362 |
| 6 | 413 | 375 |

TABLE 9

Expected Increase Feed Experiment: Titrant Usage

| Day | Control Titrant Usage (mL/day) | Restricted Glucose Titrant Usage (mL/day) |
|---|---|---|
| 0-1 | 3 | 1 |
| 1-2 | 16 | 3 |
| 2-4 | 25 | 20 |
| 4-5 | 10 | 1 |
| 5-6 | 6 | 9 |

The generally lower osmolality level (Table 8) and lower titrant usage (Table 9) in restricted-feed culture (versus the control culture) are attributable to the lower lactate amounts produced (requiring less neutralization with titrant).

In the premodeled feeds experiment, one bioreactor was set up as a control; a standard fed-batch culture was maintained in it. In addition, two restricted-feed culture test bioreactors were set up—one for "low-ramp" restricted-glucose delivery and one for "high-ramp" restricted-glucose delivery. For each test bioreactor, one syringe pump was used to increase continuously the restricted feed rate of glucose. The concentration of the glucose solution administered for the low-ramp bioreactor was 0.2 g/mL; the concentration for the high-ramp bioreactor was 0.28 g/mL.

Figure 7:
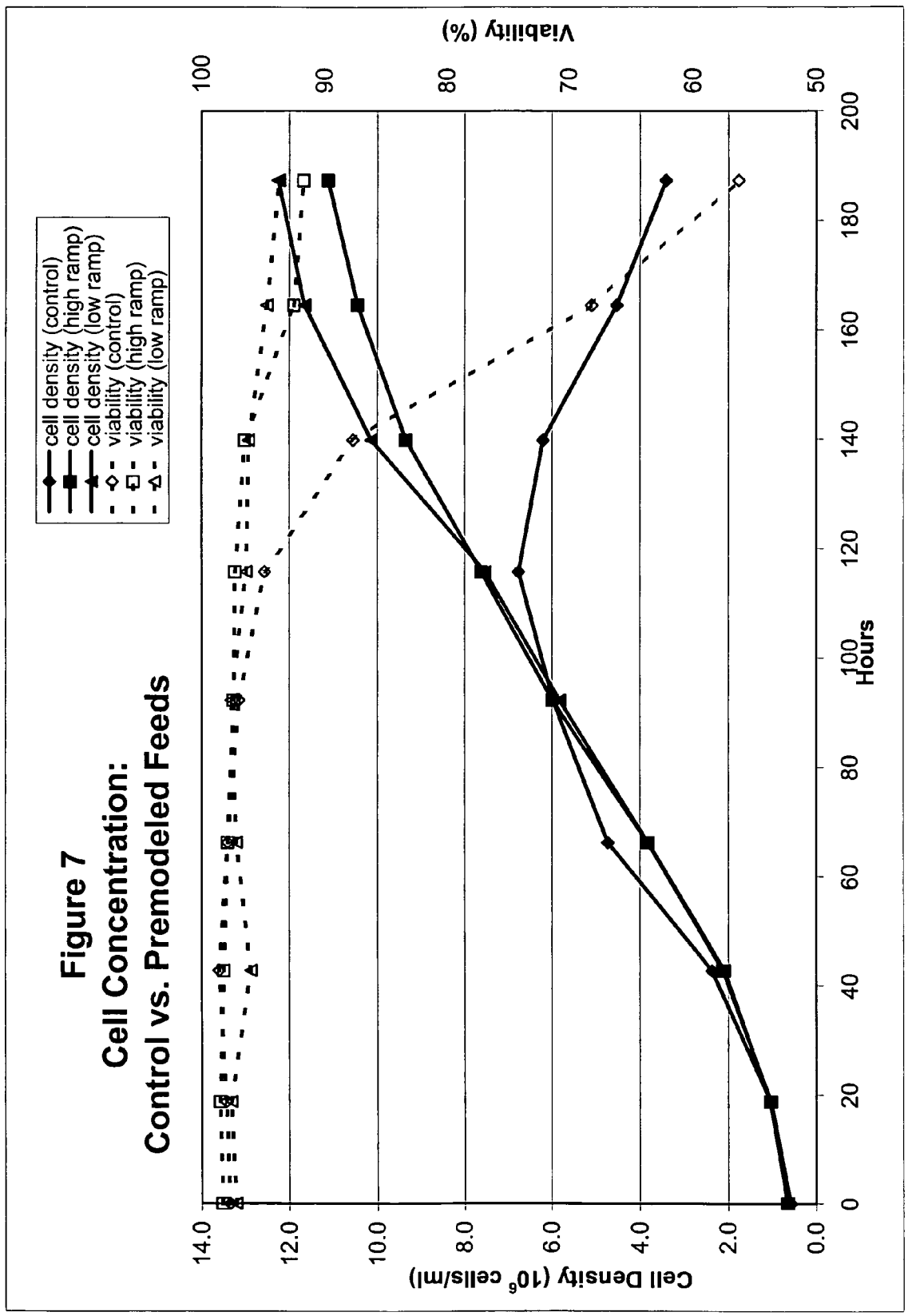
FIG. 7. Cell Concentration: Control vs. Premodeled Feeds

FIG. 7 graphically presents cell concentration (solid lines) and cell viability (dashed lines) data over culture periods in the control and test bioreactors; Table 10 presents cell growth rate data for the control and test bioreactors.

TABLE 10

Premodeled Feeds Experiment: Cell Growth Rates
(Cedex µ values per hr; Cedex µ values = cell concentration in units of $10^5$ cells per mL)

| Day | Control Rates (µ · (hr$^{-1}$)) | Low-Ramp Rates (µ · (hr$^{-1}$)) | High-Ramp Rates (µ · (hr$^{-1}$)) |
|---|---|---|---|
| 1 | 0.030 | 0.026 | 0.024 |
| 2 | 0.035 | 0.029 | 0.030 |
| 3 | 0.029 | 0.026 | 0.025 |
| 4 | 0.009 | 0.016 | 0.017 |
| 5 | 0.005 | 0.011 | 0.010 |
| 6 | -0.004 | 0.012 | 0.009 |
| 7 | -0.013 | 0.006 | 0.005 |
| 8 | -0.012 | 0.002 | 0.003 |

In both restricted-feed cultures, cell concentration continued to increase through Day 8 (192 hrs); in addition, cell viability remained at high levels through this same period (FIG. 7). In contrast, cell concentration in the control culture peaked on about Day 5 (120 hrs); a sharp drop in cell concentration, and a sharper drop in cell viability, followed (FIG.

7). The low-ramp culture reached a cell concentration of over 12×10⁶ cells/mL on Day 8, and cell viability remained higher than 90% (FIG. 7).

BMP-2 titer levels observed in restricted-feed cultures support the usefulness of methods of the invention for improving protein production from cultured animal cells (particularly for the low-ramp culture). FIG. 8 presents BMP-2 titer levels for control and test bioreactors normalized as a fraction of peak BMP-2 titer (Day 5) for the control culture. Table 11 presents BMP-2 production rates for control and test bioreactors normalized as a fraction of BMP-2 production rate of the control culture on Day 1 (as also normalized in Table 4).

TABLE 11

Premodeled Feeds Experiment:
BMP-2 Production Rate (Normalized)

| Day | Control Production Rate | Low-Ramp Production Rate | High-Ramp Production Rate |
|---|---|---|---|
| 1 | 1.00 | 1.19 | 1.17 |
| 2 | 1.01 | 0.75 | 0.77 |
| 3 | 0.94 | 0.94 | 1.02 |
| 4 | 0.67 | 0.86 | 1.02 |
| 5 | 0.16 | 1.06 | 0.56 |
| 6 | −0.19 | 1.15 | 0.59 |
| 7 | −0.39 | 0.52 | −0.02 |
| 8 | −0.02 | 0.43 | −0.03 |

The highest final titer was achieved in the low-ramp restricted-feed culture; this titer level is more than three times higher than the peak BMP-2 titer achieved in the control culture (FIG. 8). The BMP-2 production rate remained high for six days in the low-ramp culture (Table 11). The BMP-2 production rate in the high-ramp restricted-feed culture declined more quickly than the BMP-2 production rate in the low-ramp restricted-feed culture (Table 11). This more rapid decline in BMP-2 production rate is probably due to the presence of a higher level of inhibitors, such as lactate, in the high-ramp culture than in the low-ramp culture.

FIG. 9 presents profiles of glucose (solid lines) and lactate (dashed lines) concentrations (g/L) from the premodeled feeds experiment for control and test bioreactors, and Table 12 presents corresponding representative data on glucose and lactate concentrations (g/L) from this experiment. Table 13 presents glucose consumption rate data, and Table 14 presents lactate production rate data, for control and test bioreactors.

TABLE 12

Premodeled Feeds Experiment:
Glucose and Lactate Concentrations

| | | Restricted-Feed | |
|---|---|---|---|
| Hours | Control | Low-Ramp | High-Ramp |
| Glucose Concentration (g/L) | | | |
| 0 | 10.46 | 1.09 | 1.09 |
| 18.75 | 8.68 | 0.01 | 0.00 |
| 42.75 | 6.38 | 0.12 | 0.08 |
| 66.25 | 3.07 | 0.05 | 0.05 |
| 67.75 | 5.82 | — | — |
| 92.25 | 1.61 | 0.16 | 0.11 |
| 94.75 | 4.36 | — | — |
| 115.75 | 0.44 | 0.06 | 0.05 |
| 119.75 | 3.19 | — | — |
| 139.75 | 0 | 0 | 0 |
| 143.75 | 2.75 | — | — |
| 164.5 | 0.54 | 0.07 | 0.22 |
| 167.75 | 3.29 | — | — |
| 187.25 | 0.87 | 0.06 | 0.39 |
| 191 | 3.62 | — | — |
| Lactate Concentration (g/L) | | | |
| 0 | 0.01 | 0.02 | 0.01 |
| 18.75 | 1.20 | 1.06 | 1.08 |
| 42.75 | 2.90 | 1.58 | 1.88 |
| 66.25 | 4.68 | 2.06 | 2.77 |
| 67.75 | — | — | — |
| 92.25 | 5.92 | 2.20 | 3.43 |
| 94.75 | — | — | — |
| 115.75 | 7.76 | 1.86 | 3.68 |
| 119.75 | — | — | — |
| 139.75 | 8.04 | 1.24 | 4.08 |
| 143.75 | — | — | — |
| 164.5 | 7.60 | 1.18 | 4.36 |
| 167.75 | — | — | — |
| 187.25 | 7.72 | 1.09 | 4.76 |
| 191 | — | — | — |

TABLE 13

Premodeled Feeds Experiment: Glucose Consumption Rate

| Day | Control $Q_{glucose}$ (mg/10⁶ cells/day) | Low-Ramp $Q_{glucose}$ (mg/10⁶ cells/day) | High-Ramp $Q_{glucose}$ (mg/10⁶ cells/day) |
|---|---|---|---|
| 1 | 2.90 | 1.67 | 1.69 |
| 2 | 1.43 | 0.45 | 0.68 |
| 3 | 0.99 | 0.36 | 0.48 |
| 4 | 0.73 | 0.22 | 0.33 |
| 5 | 0.63 | 0.22 | 0.29 |
| 6 | 0.49 | 0.18 | 0.26 |
| 7 | 0.40 | 0.18 | 0.27 |
| 8 | 0.65 | 0.18 | 0.26 |

TABLE 14

Premodeled Feeds Experiment: Lactate Production Rate

| Day | Control $Q_{lactate}$ (mg/10⁶ cells/day) | Low-Ramp $Q_{lactate}$ (mg/10⁶ cells/day) | High-Ramp $Q_{lactate}$ (mg/10⁶ cells/day) |
|---|---|---|---|
| 1 | 1.94 | 1.61 | 1.66 |
| 2 | 1.06 | 0.35 | 0.53 |
| 3 | 0.53 | 0.17 | 0.31 |
| 4 | 0.22 | 0.03 | 0.13 |
| 5 | 0.30 | −0.05 | 0.04 |
| 6 | 0.04 | −0.07 | 0.05 |
| 7 | −0.08 | −0.01 | 0.03 |
| 8 | 0.03 | −0.01 | 0.04 |

The dashed-line profiles of FIG. 9 highlight the differences in lactate production between the three cultures. Comparing these profiles in FIG. 9 reveals that the lowest lactate levels resulted when glucose restricted-feed was set at a "low-ramp" rate. Very low lactate production rate in the restricted-feed low-ramp culture (FIG. 9 and Table 14) likely is responsible for the ability of cells in that culture to maintain such high productivity. Glucose consumption rate stabilized at about 0.2 mg/10⁶ cells/day in the low-ramp culture (Table 13).

Table 15 presents osmolality profiles for the control and restricted-feed cultures, and Table 16 presents titrant usage data for these cultures (again, per 1 L working volume).

TABLE 15

Premodeled Feeds Experiment: Osmolality

| Day | Control Osmo. (mOsm/L) | Low-Ramp Osmo. (mOsm/L) | High-Ramp Osmo. (mOsm/L) |
|---|---|---|---|
| 0 | 290 | 288 | 271 |
| 1 | 299 | 290 | 293 |
| 2 | 320 | 298 | 304 |
| 3 | 349 | 306 | 324 |
| 4 | n.a. | n.a. | n.a. |
| 5 | 408 | 296 | 334 |
| 6 | 427 | 287 | 353 |
| 7 | 437 | 221 | 308 |
| 8 | 413 | 237 | 366 |

TABLE 16

Premodeled Feeds Experiment: Titrant Usage

| Day | Control Titrant (mL/day) | Low-Ramp Titrant (mL/day) | High-Ramp Titrant (mL/day) |
|---|---|---|---|
| 1 | 1 | 0 | 5 |
| 2 | 8 | 2 | 3 |
| 3 | 10 | 2 | 4 |
| 4 | 13 | 2 | 6 |
| 5 | 10 | 1 | 4 |
| 6 | 8 | 3 | 8 |
| 7 | 5 | 1 | 2 |
| 8 | 5 | 0 | 7 |

Osmolality in the low-ramp restricted-feed culture increased marginally from a starting level of 288 mOsm/L to only 306 mOsm/L on Day 3 before settling at a level of 237 mOsm/L on Day 8 (Table 15). The low-ramp culture also required relatively little titrant from Day 1 through Day 8 (Table 16). On the other hand, osmolality in the control culture increased by almost 50% through Day 7 (Table 15), and titrant usage for the control culture always exceeded titrant usage for the low-ramp culture (Table 16). Similarly, except at Day 1 and Day 8, titrant usage for the control culture also exceeded titrant usage for the high-ramp restricted-feed culture (Table 16). As in the expected increase feed experiment, the lower osmolality level (Table 15) and generally lower titrant usage (Table 9) in the restricted-feed cultures (both low-ramp and high-ramp restricted-feed cultures) versus the control culture are attributable to the lower lactate amounts produced (requiring less neutralization with titrant) in the premodeled feeds experiment.

Feeding glucose in a restricted manner into cell culture media (and thereby keeping lactate production in the media low) had several positive effects in these experiments (particularly on protein productivity; FIG. 5 and Table 4; and FIG. 8 and Table 11). These positive effects were obtained by programming glucose deliveries to increase throughout these fed-batch cultures in order to anticipate the glucose requirements estimated for the expected or premodeled increases in glucose needs (e.g., as a result of increases in cell concentration), but all while feeding glucose in a restricted manner.

This restricted feeding strategy resulted in significant reductions in lactate production rates (throughout the expected increase feed experiment—Table 7; see also FIG. 6—and over the bulk of the premodeled feeds experiment—Table 14; see also FIG. 9) as compared to control cultures in which the cell culture medium initially contained a high level of glucose (e.g., about 10 g/L). Cell concentration (see Tables 3 and 10) and protein production levels (see Tables 4 and 11) in the restricted-feed test cultures continued to increase after these determinants peaked in control cultures. Particularly in the premodeled feeds experiment, the low-ramp restricted-feed culture achieved a final titer of recombinant protein that was more than three times higher than the peak titer of the control culture (FIG. 8).

In view of the normalized BMP2 titer levels achieved (FIG. 8), it can be seen that a key advantage of restricted-glucose feeding for controlling lactic acid production to low levels is to improve process productivity (particularly when measured in terms of protein production rates). Glucose feeding in a restricted manner for controlling lactic acid production to low levels can also facilitate process productivity when the latter is measured in terms of cell growth (FIG. 7).

Importantly, the benefits of the invention are achieved by restricted rates of glucose delivery to test cultures rather than simply by maintenance of low glucose concentrations in test cultures. For example, the glucose concentration profiles of both the low-ramp and high-ramp cultures of the premodeled feeds experiment were similarly low, but the lactate production profile of the low-ramp culture remained markedly below the lactate production profile of the high-ramp culture (FIG. 9 and Table 12). Accordingly, the beneficial metabolic profiles are the result of the adaptation of cultured animal cells for growth under culture conditions wherein glucose availability is limited by the restricted delivery of glucose to the culture, particularly where that restricted delivery is based on expected or premodeled rates of glucose consumption capacities by the cultured animal cells. No matter how many glucose transporters cultured cells express, the cells are able to obtain enough glucose to produce only low levels of lactic acid when glucose is fed to the cultures at only a restricted rate.

Example 4

Cell-Concentration-Sensor-Based System

A cell-concentration sensor that does not rely on sampling may be used to facilitate glucose delivery at restricted rates in real time. A computer monitoring system by which cell concentrations may be determined without sampling (e.g., through use of a system wherein the cell concentration of an animal cell culture is estimated through photometric measurements of culture turbidity) is programmed to record cell concentrations every five min, and to relay that data to a linked computer system that controls glucose delivery to the animal cell culture. This linked computer system is in turn programmed both to calculate a restricted glucose delivery rate and to deliver glucose to the animal cell culture at that restricted rate. This restricted rate of glucose delivery is a function of an expected or a premodeled rate of glucose consumption for cells at the estimated cell concentration.

A syringe-based glucose delivery system is set up as for the low-ramp restricted-glucose feed culture (i.e., with a 0.2 g/mL glucose feed solution) of the previous example. For cell concentrations between $1.4 \times 10^6$ cells/mL and $1.6 \times 10^6$ cells/mL in a 1 L animal cell culture system, a restricted rate of glucose delivery to a culture is determined to be (as a function of an expected or a premodeled rate of glucose consumption) 8.4 mg glucose/hr, whereas for cell concentrations between $1.9 \times 10^6$ cells/mL and $2.1 \times 10^6$ cells/mL in a 1 L animal cell culture system, a restricted rate of glucose delivery to a culture is determined to be (again as a function of an expected or a premodeled rate of glucose consumption) 11 mg glucose/hr. Accordingly, when the computer monitoring system measures cell concentration to be approximately $1.5 \times 10^6$ cells/mL, the linked computer system that controls glucose delivery to the animal cell culture adjusts in real time the rate of glucose delivery to the culture so that the syringe delivers 0.042 mL/hr of the 0.2 g/mL glucose feed solution (i.e., glucose is delivered to the cell culture system at a rate of 8.4 mg/hr). Later, when the computer monitoring system measures cell concentration to be approximately $2.0 \times 10^6$ cells/mL, the linked computer system that controls glucose delivery to the animal cell culture adjusts in real time the rate of glucose delivery to the culture so that the syringe delivers 0.055 mL/hr of the 0.2 g/mL glucose feed solution (i.e., glucose is delivered to the cell culture system at a rate of 11 mg/hr).

The above-described invention for the restricted feeding of glucose into cell cultures provides a practical method for improving culture performance of animal cells. This practical method provides a straightforward option for improving industrial-scale cell culture.

The foregoing detailed description and examples have been given for clarity of understanding only. No unnecessary limitations are to be understood therefrom. The invention is not limited to the exact details shown and described, for variation ascertainable to one skilled in the art will be included within the invention defined by the claims.

We claim:

1. A cell culture method for controlling lactic acid production to low levels in a fed-batch cell culture comprising:
   mixing animal cells and a medium to form a cell culture; and
   feeding glucose in a restricted manner to the cell culture, wherein feeding glucose in a restricted manner comprises providing glucose to the cell culture at a rate that is a function of an expected rate of glucose consumption by the animal cells cultured in medium containing a high level of glucose, wherein the function is a multiplication of the expected rate by a percentage less than 100%, and
   wherein feeding glucose in a restricted manner comprises feeding glucose without feedback control sampling during culture.

2. The method of claim 1, wherein the percentage is at least 33%.

3. The method of claim 1, wherein the percentage is no more than 45%.

4. The method of claim 1, wherein feeding glucose in a restricted manner comprises the addition of one or more boluses of glucose feed.

5. The method of claim 1, wherein a sensor is used to monitor cell concentration in the cell culture, and a cell-concentration-sensor-derived measurement is additionally used in calculating the rate of feeding glucose in a restricted manner to the cell culture.

6. The method of claim 1, wherein a pH sensor is used to monitor pH of the cell culture, and, in response to a rise above a predetermined pH value, additional glucose is fed in a restricted manner to the cell culture.

7. The method of claim 6, wherein the additional glucose fed in a restricted manner comprises one or more boluses of glucose feed.

8. The method of claim 6, wherein the predetermined pH value is approximately 7.

9. The method of claim 1, wherein a pH sensor is used to monitor pH of the cell culture, and, in response to a rise above a predetermined pH value, feeding glucose in a restricted manner subsequently continues at a new rate that is greater than an immediately prior rate.

10. The method of claim 9, wherein the new rate is greater by at least 15% over the immediately prior rate.

11. The method of claim 9, wherein the new rate is greater by no more than 50% over the immediately prior rate.

12. The method of claim 9, wherein the response to a rise above a predetermined pH value further comprises addition of one or more boluses of glucose feed to the cell culture.

13. The method of claim 9, wherein the predetermined pH value is approximately 7.

14. The method of claim 1, wherein feeding glucose without feedback control sampling during culture comprises:
   (i) using a cell-concentration sensor to monitor cell concentration in the cell culture without sampling, and additionally using a cell-concentration-sensor-derived measurement in calculating the rate of feeding glucose in a restricted manner to the cell culture;
   (ii) using a pH sensor to monitor pH of the cell culture without sampling, and, in response to a rise above a predetermined pH value, subsequently feeding glucose in a restricted manner at a new rate that is greater than an immediately prior rate; or
   (iii) using both the cell-concentration sensor and the pH sensor as described in (i) and (ii), respectively.

15. The method of claim 14, wherein the response to a rise above a predetermined pH value in (ii) and/or (iii) further comprises addition of one or more boluses of glucose feed to the cell culture.

16. The method of claim 14, wherein the predetermined pH value is approximately 7.

17. A cell culture method for controlling lactic acid production to low levels in a fed-batch cell culture comprising:
   (a) mixing animal cells and a medium containing a high level of glucose to form a first cell culture;
   (b) determining a glucose consumption rate for the animal cells cultured in the first cell culture;
   (c) mixing animal cells and a medium to form a second cell culture; and
   (d) feeding glucose in a restricted manner to the second cell culture at a rate that is a function of the determined glucose consumption rate of step (b),
   wherein the function is a multiplication of the determined rate by a percentage less than 100%, and wherein feeding glucose in a restricted manner comprises feeding glucose without feedback control sampling during culture.

18. The method of claim 17, wherein the percentage is at least 33%.

19. The method of claim 17, wherein the percentage is no more than 45%.

20. The method of claim 17, wherein a sensor is used to monitor cell concentration in the second cell culture, and a cell-concentration-sensor-derived measurement is additionally used in calculating the rate of feeding glucose in a restricted manner to the second cell culture.

21. The method of claim 17, wherein a pH sensor is used to monitor pH of the second cell culture, and, in response to a rise above a predetermined pH value, feeding glucose in a restricted manner to the second cell culture subsequently continues at a new rate that is greater than an immediately prior rate.

22. The method of claim 21, wherein the predetermined pH value is approximately 7.

23. The method of claim 21, wherein the new rate is greater by at least 15% over the immediately prior rate.

24. The method of claim 21, wherein the new rate is greater by no more than 50% over the immediately prior rate.

25. The method of claim 17, wherein a pH sensor is used to monitor pH of the second cell culture, and, in response to a rise above a predetermined pH value, feeding glucose in a restricted manner further comprises addition of one or more boluses of glucose feed to the second cell culture.

26. The method of claim 25, wherein feeding glucose in a restricted manner to the second cell culture further comprises subsequently continuing the feeding at a new rate that is greater than an immediately prior rate.

27. The method of claim 25, wherein the predetermined pH value is approximately 7.

28. The method of claim 26, wherein the new rate is greater by at least 15% over the immediately prior rate.

29. The method of claim 26, wherein the new rate is greater by no more than 50% over the immediately prior rate.

30. The method of claim 17, wherein feeding glucose without feedback control sampling during culture comprises:
   (i) using a cell-concentration sensor to monitor cell concentration in the second cell culture without sampling, and additionally using a cell-concentration-sensor-derived measurement in calculating the rate of feeding glucose in a restricted manner to the second cell culture;
   (ii) using a pH sensor to monitor pH of the second cell culture without sampling, and, in response to a rise above a predetermined pH value, subsequently feeding glucose in a restricted manner at a new rate that is greater than an immediately prior rate; or
   (iii) using both the cell-concentration sensor and the pH sensor as described in (i) and (ii), respectively.

31. The method of claim 30, wherein the response to a rise above a predetermined pH value in (ii) and/or (iii) further comprises addition of one or more boluses of glucose feed to the second cell culture.

32. The method of claim 30, wherein the predetermined pH value is approximately 7.

* * * * *